United States Patent
Birdsall

(10) Patent No.: US 7,524,331 B2
(45) Date of Patent: Apr. 28, 2009

(54) CATHETER DELIVERED VALVE HAVING A BARRIER TO PROVIDE AN ENHANCED SEAL

(75) Inventor: Matthew J. Birdsall, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 373 days.

(21) Appl. No.: 11/278,925

(22) Filed: Apr. 6, 2006

(65) Prior Publication Data

US 2007/0239265 A1 Oct. 11, 2007

(51) Int. Cl.
*A61F 2/06* (2006.01)

(52) U.S. Cl. .................. 623/2.11; 623/1.24

(58) Field of Classification Search .............. 623/1.24, 623/2.1–2.19
See application file for complete search history.

(56) References Cited

U.S. PATENT DOCUMENTS

| | | |
|---|---|---|
| 3,334,629 A | 8/1967 | Cohn |
| 3,540,431 A | 11/1970 | Mobin-Uddin |
| 3,628,535 A | 12/1971 | Ostrowsky et al. |
| 3,642,004 A | 2/1972 | Osthagen et al. |
| 3,657,744 A | 4/1972 | Esek |
| 3,671,979 A | 6/1972 | Moulopoulos |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 4,056,854 A | 11/1977 | Boretos et al. |
| 4,106,129 A | 8/1978 | Carpentier et al. |
| 4,233,690 A | 11/1980 | Akins |
| 4,291,420 A | 9/1981 | Reul |
| 4,425,908 A | 1/1984 | Simon |
| 4,501,030 A | 2/1985 | Lane |
| 4,580,568 A | 4/1986 | Gianturco |
| 4,610,688 A | 9/1986 | Silvestrini et al. |
| 4,647,283 A | 3/1987 | Carpentier et al. |
| 4,648,881 A | 3/1987 | Carpentier et al. |
| 4,655,771 A | 4/1987 | Wallsten |
| 4,662,885 A | 5/1987 | DiPisa, Jr. |
| 4,665,906 A | 5/1987 | Jervis |

(Continued)

FOREIGN PATENT DOCUMENTS

EP 1057459 2/2000

(Continued)

OTHER PUBLICATIONS

P. Bonhoeffer, MD, et al., "Transcatheter Implantation of a Bovine Valve in a Pulmonary Position—A Lamb Study," pp. 8-3-816; Aug. 2000.

(Continued)

*Primary Examiner*—Suzette J Gherbi

(57) ABSTRACT

A system for treating abnormalities of the right ventricular outflow tract includes a prosthetic valve device having a barrier material contacting at least a portion of the outer surface of the valve device. One embodiment of the invention includes a barrier member attached to the exterior surface of the valve device. Another embodiment includes a barrier material that is injected within the vascular system. Yet another embodiment of the invention includes a method for replacing a pulmonary valve that includes forming a barrier around the outer surface of a replacement valve and preventing blood flow around the replacement valve.

12 Claims, 6 Drawing Sheets

U.S. PATENT DOCUMENTS

| | | |
|---|---|---|
| 4,710,192 A | 12/1987 | Liotta et al. |
| 4,733,665 A | 3/1988 | Palmaz |
| 4,819,751 A | 4/1989 | Shimada et al. |
| 4,834,755 A | 5/1989 | Silverstrini et al. |
| 4,856,516 A | 8/1989 | Hillstead |
| 4,872,874 A | 10/1989 | Taheri |
| 4,909,252 A | 3/1990 | Goldberger |
| 4,917,102 A | 4/1990 | Miller et al. |
| 4,954,126 A | 9/1990 | Wallsten |
| 4,994,077 A | 2/1991 | Dobben |
| 5,002,559 A | 3/1991 | Tower |
| 5,156,621 A | 10/1992 | Navia et al. |
| 5,161,547 A | 11/1992 | Tower |
| 5,163,953 A | 11/1992 | Vince |
| 5,197,979 A | 3/1993 | Quintero et al. |
| 5,217,483 A | 6/1993 | Tower |
| 5,332,402 A | 7/1994 | Teitelbaum et al. |
| 5,336,258 A | 8/1994 | Quintero et al. |
| 5,350,398 A | 9/1994 | Pavcnik et al. |
| 5,370,685 A | 12/1994 | Stevens |
| 5,389,106 A | 2/1995 | Tower |
| 5,397,351 A | 3/1995 | Pavcnik et al. |
| 5,411,552 A | 5/1995 | Andersen et al. |
| 5,431,676 A | 7/1995 | Dubrul et al. |
| 5,507,767 A | 4/1996 | Maeda et al. |
| 5,545,211 A | 8/1996 | An et al. |
| 5,554,185 A | 9/1996 | Block et al. |
| 5,575,818 A | 11/1996 | Pinchuk |
| 5,645,559 A | 7/1997 | Hachtman et al. |
| 5,667,523 A | 9/1997 | Bynon et al. |
| 5,674,277 A | 10/1997 | Freitag |
| 5,693,085 A * | 12/1997 | Buirge et al. ............... 623/1.13 |
| 5,695,498 A | 12/1997 | Tower |
| 5,713,953 A | 2/1998 | Vallana et al. |
| 5,800,456 A | 9/1998 | Maeda et al. |
| 5,817,126 A | 10/1998 | Imran |
| 5,824,043 A | 10/1998 | Cottone, Jr. |
| 5,824,053 A | 10/1998 | Khosravi et al. |
| 5,824,056 A | 10/1998 | Rosenberg |
| 5,824,064 A | 10/1998 | Taheri |
| 5,840,081 A | 11/1998 | Andersen et al. |
| 5,855,597 A | 1/1999 | Jayaraman |
| 5,855,601 A | 1/1999 | Bessler et al. |
| 5,860,996 A | 1/1999 | Tower |
| 5,861,028 A | 1/1999 | Angell |
| 5,868,783 A | 2/1999 | Tower |
| 5,876,448 A | 3/1999 | Thompson et al. |
| 5,888,201 A | 3/1999 | Stinson et al. |
| 5,891,191 A | 4/1999 | Stinson |
| 5,907,893 A | 6/1999 | Zadno-Azizi et al. |
| 5,925,063 A | 7/1999 | Khosravi |
| 5,944,738 A | 8/1999 | Amplatz et al. |
| 5,954,766 A | 9/1999 | Zadno-Aziz et al. |
| 5,957,949 A | 9/1999 | Leonhardt et al. |
| 5,984,957 A | 11/1999 | Laptewicz, Jr. et al. |
| 6,001,126 A | 12/1999 | Nguyen-Thien-Nhon |
| 6,027,525 A | 2/2000 | Suh et al. |
| 6,042,598 A | 3/2000 | Tsugita et al. |
| 6,051,014 A | 4/2000 | Jang |
| 6,123,723 A | 9/2000 | Konya et al. |
| 6,146,366 A | 11/2000 | Schachar |
| 6,162,245 A | 12/2000 | Jayaraman |
| 6,168,614 B1 | 1/2001 | Andersen et al. |
| 6,200,336 B1 | 3/2001 | Pavcnik et al. |
| 6,221,006 B1 | 4/2001 | Dubrul et al. |
| 6,221,091 B1 | 4/2001 | Khosravi |
| 6,241,757 B1 | 6/2001 | An et al. |
| 6,254,436 B1 | 7/2001 | Nitta et al. |
| 6,258,114 B1 | 7/2001 | Konya et al. |
| 6,258,115 B1 | 7/2001 | Dubrul et al. |
| 6,258,120 B1 | 7/2001 | McKenzie et al. |
| 6,277,555 B1 | 8/2001 | Duran et al. |
| 6,309,417 B1 | 10/2001 | Spence et al. |
| 6,327,772 B1 | 12/2001 | Zadno-Aziz et al. |
| 6,338,735 B1 | 1/2002 | Stevens |
| 6,342,070 B1 | 1/2002 | Nguyen-Thien-Nhon |
| 6,348,063 B1 | 2/2002 | Yassour et al. |
| 6,350,282 B1 | 2/2002 | Eberhardt |
| 6,352,708 B1 | 3/2002 | Duran et al. |
| 6,364,905 B1 | 4/2002 | Simpson et al. |
| 6,371,970 B1 | 4/2002 | Khosravi et al. |
| 6,371,983 B1 | 4/2002 | Lane |
| 6,379,383 B1 | 4/2002 | Palmaz et al. |
| 6,398,807 B1 | 6/2002 | Chouinard et al. |
| 6,409,750 B1 | 6/2002 | Hyodoh et al. |
| 6,425,916 B1 | 7/2002 | Garrison et al. |
| 6,440,164 B1 | 8/2002 | DiMatteo et al. |
| 6,458,153 B1 | 10/2002 | Bailey et al. |
| 6,468,303 B1 | 10/2002 | Amplatz et al. |
| 6,475,239 B1 | 11/2002 | Campbell |
| 6,482,228 B1 | 11/2002 | Norred |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,509,930 B1 | 1/2003 | Hirano et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,558,417 B2 | 5/2003 | Peredo |
| 6,562,058 B2 | 5/2003 | Seguin et al. |
| 6,569,196 B1 | 5/2003 | Vesely |
| 6,592,546 B1 | 7/2003 | Barbut et al. |
| 6,622,604 B1 | 9/2003 | Chouinard et al. |
| 6,632,243 B1 | 10/2003 | Zadno-Azizi et al. |
| 6,635,068 B1 | 10/2003 | Dubrul et al. |
| 6,652,571 B1 | 11/2003 | White et al. |
| 6,652,578 B2 | 11/2003 | Bailey et al. |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,702,851 B1 | 3/2004 | Chinn et al. |
| 6,719,789 B2 | 4/2004 | Cox |
| 6,730,118 B2 | 5/2004 | Spenser et al. |
| 6,730,377 B2 | 5/2004 | Wang |
| 6,733,525 B2 | 5/2004 | Uamg et al. |
| 6,736,846 B2 | 5/2004 | Cox |
| 6,752,828 B2 | 6/2004 | Thornton |
| 6,758,855 B2 | 7/2004 | Fulton, III et al. |
| 6,769,434 B2 | 8/2004 | Streeter at et al. |
| 6,887,266 B2 | 5/2005 | Williams et al. |
| 6,890,330 B2 | 5/2005 | Streeter et al. |
| 6,896,690 B1 | 5/2005 | Lambrecht et al. |
| 6,929,653 B2 | 8/2005 | Streeter |
| 7,270,675 B2 * | 9/2007 | Chun et al. ............... 623/1.15 |
| 2001/0007956 A1 | 7/2001 | Letac et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2002/0032480 A1 | 3/2002 | Spence et al. |
| 2002/0032481 A1 | 3/2002 | Gabbay |
| 2002/0052651 A1 | 5/2002 | Myers et al. |
| 2002/0058995 A1 | 5/2002 | Stevens |
| 2002/0077696 A1 | 6/2002 | Zadno-Azizi et al. |
| 2002/0095209 A1 | 7/2002 | Zadno-Azizi et al. |
| 2002/0111674 A1 | 8/2002 | Chouinard et al. |
| 2002/0151970 A1 | 10/2002 | Garrison et al. |

| | | | | | |
|---|---|---|---|---|---|
| 2002/0161392 A1 | 10/2002 | Dubrul | EP | 0810913 | 6/2004 |
| 2002/0161394 A1 | 10/2002 | Macoviak et al. | EP | 1229864 B1 | 4/2005 |
| 2002/0193871 A1 | 12/2002 | Beyersdorf et al. | FR | 2 826 863 | 1/2003 |
| 2003/0014104 A1 | 1/2003 | Cribier | WO | WO 93/15693 | 8/1993 |
| 2003/0023303 A1 | 1/2003 | Palmaz et al. | WO | WO 95/04556 | 2/1995 |
| 2003/0028247 A1 | 2/2003 | Cali | WO | WO 95/29640 | 11/1995 |
| 2003/0036791 A1 | 2/2003 | Philipp et al. | WO | WO 96/14032 | 5/1996 |
| 2003/0040771 A1 | 2/2003 | Hyodoh et al. | WO | WO 98/36790 | 8/1998 |
| 2003/0040772 A1 | 2/2003 | Hyodoh et al. | WO | WO 00/09059 | 2/2000 |
| 2003/0055495 A1 | 3/2003 | Pease et al. | WO | WO 00/44308 | 8/2000 |
| 2003/0069635 A1 | 4/2003 | Cartledge et al. | WO | WO 00/44313 | 8/2000 |
| 2003/0109924 A1 | 6/2003 | Cribier | WO | WO 00/67661 | 11/2000 |
| 2003/0125795 A1 | 7/2003 | Pavcnik et al. | WO | WO 01/05331 | 1/2001 |
| 2003/0125805 A1 | 7/2003 | Johnson et al. | WO | WO 01/35870 | 5/2001 |
| 2003/0130729 A1 | 7/2003 | Paniagua et al. | WO | WO 01/64137 | 9/2001 |
| 2003/0149475 A1 | 8/2003 | Hyodoh et al. | WO | WO 02/36048 | 5/2002 |
| 2003/0149476 A1 | 8/2003 | Damm et al. | WO | WO 02/100297 | 12/2002 |
| 2003/0149478 A1 | 8/2003 | Figulla et al. | WO | WO 03/003943 | 1/2003 |
| 2003/0153974 A1 | 8/2003 | Spenser et al. | WO | WO 03/003949 | 1/2003 |
| 2003/0181850 A1 | 9/2003 | Diamond et al. | WO | WO 03/011195 | 2/2003 |
| 2003/0199913 A1 | 10/2003 | Dubrul et al. | WO | WO 03/015851 | 2/2003 |
| 2003/0199963 A1 | 10/2003 | Tower et al. | WO | WO 2004/019811 | 3/2004 |
| 2003/0199972 A1 | 10/2003 | Zadno-Aziz et al. | WO | WO 2004/023980 | 3/2004 |
| 2003/0212452 A1 | 11/2003 | Zadno-Aziz et al. | WO | WO 2004/041126 | 5/2004 |
| 2003/0212454 A1 | 11/2003 | Scott et al. | WO | WO 2004/047681 | 6/2004 |
| 2004/0034411 A1 | 2/2004 | Quijano et al. | WO | WO 2005/013860 | 2/2005 |
| 2004/0039436 A1 | 2/2004 | Spenser et al. | | | |
| 2004/0049224 A1 | 3/2004 | Buehlmann et al. | | | |
| 2004/0049262 A1 | 3/2004 | Obermiller et al. | | | |
| 2004/0049266 A1 | 3/2004 | Anduiza et al. | | | |
| 2004/0082904 A1 | 4/2004 | Houde et al. | | | |
| 2004/0088045 A1 | 5/2004 | Cox | | | |
| 2004/0098112 A1 | 5/2004 | DiMatteo et al. | | | |
| 2004/0111096 A1 | 6/2004 | Tu et al. | | | |
| 2004/0116951 A1 | 6/2004 | Rosengart | | | |
| 2004/0117004 A1 | 6/2004 | Osborne et al. | | | |
| 2004/0122468 A1 | 6/2004 | Yodfat et al. | | | |
| 2004/0127979 A1 | 7/2004 | Wilson | | | |
| 2004/0138742 A1 | 7/2004 | Myers et al. | | | |
| 2004/0138743 A1 | 7/2004 | Myers et al. | | | |
| 2004/0186563 A1 | 9/2004 | Lobbi | | | |
| 2004/0215339 A1 | 10/2004 | Drasler et al. | | | |
| 2005/0085841 A1 | 4/2005 | Eversull et al. | | | |
| 2005/0085842 A1 | 4/2005 | Eversull et al. | | | |
| 2005/0085843 A1 | 4/2005 | Opolski et al. | | | |
| 2005/0085890 A1 | 4/2005 | Rasumssen et al. | | | |
| 2005/0096692 A1 | 5/2005 | Linder et al. | | | |
| 2005/0096734 A1 | 5/2005 | Majercak et al. | | | |
| 2005/0096735 A1 | 5/2005 | Hojeibane et al. | | | |
| 2005/0096738 A1 | 5/2005 | Cali et al. | | | |
| 2005/0209065 A1 | 9/2005 | Schlosser | | | |
| 2005/0251251 A1 | 11/2005 | Cribier | | | |
| 2006/0052867 A1 | 3/2006 | Revuelta et al. | | | |
| 2006/0247762 A1* | 11/2006 | Acosta et al. ............. 623/1.24 | | | |

FOREIGN PATENT DOCUMENTS

| | | |
|---|---|---|
| EP | 0937439 B1 | 9/2003 |
| EP | 1340473 | 9/2003 |
| EP | 1356793 | 10/2003 |

OTHER PUBLICATIONS

P. Bonhoeffer, MD et al., "Percutaneous Replacement of Pulmonary Valve in a Right-Ventricle to Pulmonary-Artery Prosthetic Conduit with Valve Dysfunction," pp. 1403-1405; Oct. 2000.

Y. Boudjemline, MD, et al., "Steps Towards Percutaneous Aortic Valve Replacement," pp. 775-778; Feb. 2002.

P. Bonhoeffer, MD, et al., "Percutaneous Insertion of the Pulmonary Valve," Journal of the American College of Cardiology, vol. 39, No. 10, pp. 1664-1669; Feb. 2002.

A Cribier, MD, et al., "Percutaneous Transcatheter Implantation of an Aortic Valve Prosthesis for Calcific Aortic Stenosis—First Human Description," pp. 3006-3008; Dec. 2002.

A. Cribier, MD, et al.; "Early Experience with Percutaneous Transcatheter Implantation of Heart Valve Prosthesis for the Treatment of End-Stage Inoperable Patients with Calcific Aortic Stenosis," Journal of the American College of Cardiology, vol. 43, No. 4, pp. 698-703; Nov. 2003.

Y. Boudjemline, MD. et al., "Percutaneous Pulmonary Valve Replacement in a Large Right Ventricular Outflow Tract," Journal of the American College of Cardiology, vol. 43, No. 6: pp. 1082-1087; Mar. 2004.

Andersen, H.R. et al, "Tran luminal implantation of artificial heart valves. Description of a new expandable aortic valve and initial results with implantation by catheter technique in closed chest pigs." Euro. Heart J. (1992) 13:704-708.

Bonhoeffer, "Percutaneous insertion of the pulmonary valve," Journal of American College of Cardiology Foundation, (2002) 39(0):1664-1669.

Iliopoulos, et al., "Repeat replacement of aortic valve bioprosthesis," Ann. Thorac Surg. (1995), 59:1217-1219.

* cited by examiner

CATHETER DELIVERED VALVE HAVING A BARRIER TO PROVIDE AN ENHANCED SEAL

TECHNICAL FIELD

This invention relates generally to medical devices for treating cardiac valve abnormalities, and particularly to a pulmonary valve replacement system and method of employing the same.

BACKGROUND OF THE INVENTION

Heart valves, such as the mitral, tricuspid, aortic and pulmonary valves, are sometimes damaged by disease or by aging, resulting in problems with the proper functioning of the valve. Heart valve problems generally take one of two forms: stenosis, in which a valve does not open completely or the opening is too small, resulting in restricted blood flow; or insufficiency, in which blood leaks backward across a valve when it should be closed.

The pulmonary valve regulates blood flow between the right ventricle and the pulmonary artery, controlling blood flow between the heart and the lungs. Pulmonary valve stenosis is frequently due to a narrowing of the pulmonary valve or the pulmonary artery distal to the valve. This narrowing causes the right side of the heart to exert more pressure to provide sufficient flow to the lungs. Over time, the right ventricle enlarges, which leads to congestive heart failure (CHF). In severe cases, the CHF results in clinical symptoms including shortness of breath, fatigue, chest pain, fainting, heart murmur, and in babies, poor weight gain. Pulmonary valve stenosis most commonly results from a congenital defect, and is present at birth, but is also associated with rheumatic fever, endocarditis, and other conditions that cause damage to or scarring of the pulmonary valve. Valve replacement may be required in severe cases to restore cardiac function.

Previously, valve repair or replacement required open-heart surgery with its attendant risks, expense, and extended recovery time. Open-heart surgery also requires cardiopulmonary bypass with risk of thrombosis, stroke, and infarction. More recently, flexible valve prostheses and various delivery devices have been developed so that replacement valves can be implanted transvenously using minimally invasive techniques. As a consequence, replacement of the pulmonary valve has become a treatment option for pulmonary valve stenosis.

The most severe consequences of pulmonary valve stenosis occur in infants and young children when the condition results from a congenital defect. Frequently, the pulmonary valve must be replaced with a prosthetic valve when the child is young, usually less than five years of age. However, as the child grows, the valve can become too small to accommodate the blood flow to the lungs that is needed to meet the increasing energy demands of the growing child, and it may then need to be replaced with a larger valve. Alternatively, in a patient of any age, the implanted valve may fail to function properly due to calcium buildup and have to be replaced. In either case, repeated surgical or transvenous procedures are required.

To address the need for pulmonary valve replacement, various implantable pulmonary valve prostheses, delivery devices and surgical techniques have been developed and are presently in use. One such prosthesis is a bioprosthetic, valved conduit comprising a glutaraldehyde treated bovine jugular vein containing a natural, trileaflet venous valve, and sinus. A similar device is composed of a porcine aortic valve sutured into the center of a woven fabric conduit. A common conduit used in valve replacement procedures is a homograft, which is a vessel harvested from a cadaver. Valve replacement using either of these devices requires thoracotomy and cardiopulmonary bypass.

When the valve in the prostheses must be replaced, for the reasons described above or other reasons, an additional surgery is required. Because many patients undergo their first procedure at a very young age, they often undergo numerous procedures by the time they reach adulthood. These surgical replacement procedures are physically and emotionally taxing, and a number of patients choose to forgo further procedures after they are old enough to make their own medical decisions.

Recently, implantable stented valves have been developed that can be delivered transvenously using a catheter-based delivery system. These stented valves comprise a collapsible valve attached to the interior of a tubular frame or stent. The valve can be any of the valve prostheses described above, or it can be any other suitable valve. In the case of valves in harvested vessels, the vessel can be of sufficient length to extend beyond both sides of the valve such that it extends to both ends of the valve support stent.

The stented valves can also comprise a tubular portion or "stent graft" that can be attached to the interior or exterior of the stent to provide a generally tubular internal passage for the flow of blood when the leaflets are open. The graft can be separate from the valve and it can be made from any suitable biocompatible material including, but not limited to, fabric, a homograft, porcine vessels, bovine vessels, and equine vessels.

The stent portion of the device can be reduced in diameter, mounted on a catheter, and advanced through the circulatory system of the patient. The stent portion can be either self-expanding or balloon expandable. In either case, the stented valve can be positioned at the delivery site, where the stent portion is expanded against the wall of a previously implanted prostheses or a native vessel to hold the valve firmly in place.

One embodiment of a stented valve is disclosed in U.S. Pat. No. 5,957,949 titled "Percutaneous Placement Valve Stent" to Leonhardt, et al, the contents of which are incorporated herein by reference.

Over time, implanted prosthetic conduits and valves are frequently subject to calcification, causing the affected conduit or valve to lose flexibility, become misshapen, and fail to function effectively. Furthermore, because they are long term implants, synthetic conduits sometimes undergo longitudinal stretching or fibrotic ingrowth of the tissue surrounding the conduit. In either case, the conduit can become so distorted that blood flow is impeded or the valve is misaligned, allowing blood to flow around the periphery of the valve.

An additional drawback of using a stented valve is that the stents are often difficult to properly position within a conduit resulting in a misplaced valve. Additionally, stented valves may migrate along the conduit after implantation due to forces applied by the blood flow through the vessel.

It would be desirable, therefore, to provide an implantable pulmonary valve that can readily be replaced, and that would overcome the limitations and disadvantages inherent in the devices described above.

SUMMARY OF THE INVENTION

It is an object of the present invention to provide a vascular valve replacement system having at least a delivery catheter and a replacement valve device disposed on the delivery catheter. The replacement valve device includes a prosthetic valve connected to a valve support region of an expandable support structure. The valve support region includes a plurality of protective struts disposed between a first stent region and a second stent region.

The system and the prosthetic valve will be described herein as being used for replacing a pulmonary valve. The pulmonary valve is also known to those having skill in the art as the "pulmonic valve" and as used herein, those terms shall be considered to mean the same thing.

Thus, one aspect of the present invention provides a system for treating abnormalities of the right ventricular outflow tract comprising a conduit, a catheter and a prosthetic valve device. The prosthetic valve device comprises a valve connected to a support structure and a barrier member contacting at least a portion of the outer surface of the support structure of the valve device. When the valve device is deployed from the catheter and situated within the conduit, the barrier material prevents blood flow between the inner wall of the conduit and the outer surface of the support structure of the valve device.

Another aspect of the invention provides a pulmonary valve replacement system comprising a conduit, a prosthetic valve device and a barrier material. The valve device is positioned within the conduit and the barrier is deployed from a catheter. When the barrier material is placed between the conduit and the outer surface of the support structure of the valve device to prevent blood flow around the valve device.

Another aspect of the invention provides a pulmonary valve replacement system comprising a conduit, and a prosthetic valve device having a barrier member disposed about at least a portion of the support structure of the valve device. When the valve device is positioned within the lumen of the conduit, the barrier member contacts the surface of the interior wall of the conduit and prevents blood flow around the valve device.

Another aspect of the invention provides a method for replacing a pulmonary valve. The method comprises using a catheter to deliver a pulmonary valve device to a treatment site within a conduit. The pulmonary valve device includes a valve connected to a support structure and a barrier material disposed about at least a portion of the outer surface of the support structure. The method further comprises deploying the valve device from the catheter, positioning the valve device within the conduit and forming a barrier and thereby preventing blood flow around the support structure.

The present invention is illustrated by the accompanying drawings of various embodiments and the detailed description given below. The drawings should not be taken to limit the invention to the specific embodiments, but are for explanation and understanding. The detailed description and drawings are merely illustrative of the invention rather than limiting, the scope of the invention being defined by the appended claims and equivalents thereof. The drawings are not to scale. The foregoing aspects and other attendant advantages of the present invention will become more readily appreciated by the detailed description taken in conjunction with the accompanying drawings.

DETAILED DESCRIPTION

The invention will now be described by reference to the drawings wherein like numbers refer to like structures.

Figure 1:
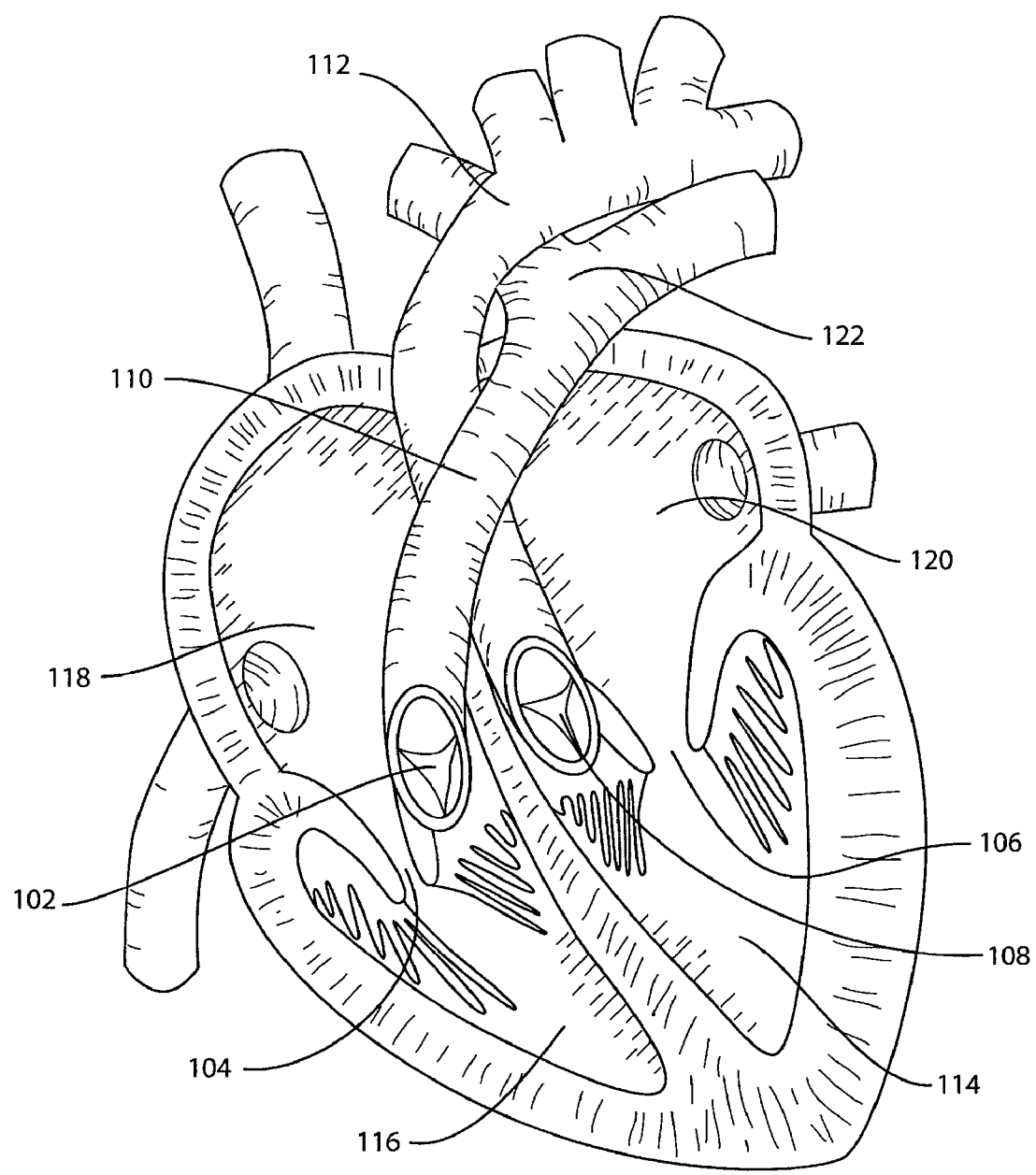
FIG. 1 is a schematic interior view of a human heart showing the functioning of the four heart valves.

Referring to the drawings, FIG. 1 is a schematic representation of the interior of human heart 100. Human heart 100 includes four valves that work in synchrony to control the flow of blood through the heart. Tricuspid valve 104, situated between right atrium 118 and right ventricle 116, and mitral valve 106, between left atrium 120 and left ventricle 114 facilitate filling of ventricles 116 and 114 on the right and left sides, respectively, of heart 100. Aortic valve 108 is situated at the junction between aorta 112 and left ventricle 114 and facilitates blood flow from heart 100, through aorta 112 to the peripheral circulation.

Pulmonary valve 102 is situated at the junction of right ventricle 116 and pulmonary artery 110 and facilitates blood flow from heart 100 through the pulmonary artery 110 to the lungs for oxygenation. The four valves work by opening and closing in harmony with each other. During diastole, tricuspid valve 104 and mitral valve 106 open and allow blood flow into ventricles 114 and 116, and the pulmonic valve and aortic valve are closed. During systole, shown in FIG. 1, aortic valve 108 and pulmonary valve 102 open and allow blood flow from left ventricle 114, and right ventricle 116 into aorta 112 and pulmonary 110, respectively.

The right ventricular outflow tract is the segment of pulmonary artery 110 that includes pulmonary valve 102 and extends to branch point 122, where pulmonary artery 110 forms left and right branches that carry blood to the left and right lungs respectively. A defective pulmonary valve or other abnormalities of the pulmonary artery that impede blood flow from the heart to the lungs sometimes require surgical repair or replacement of the right ventricular outflow tract with prosthetic conduit 202, as shown in FIG. 2A-C.

Such conduits comprise tubular structures of biocompatible materials, with a hemocompatible interior surface. Examples of appropriate biocompatible materials include polytetrafluoroethylene (PTFE), woven polyester fibers such as Dacron® fibers (E.I. Du Pont De Nemours & Co., Inc.), and bovine vein crosslinked with glutaraldehyde. One common conduit is a homograft, which is a vessel harvested from a cadaver and treated for implantation into a recipient's body.

These conduits may contain a valve at a fixed position within the interior lumen of the conduit that functions as a replacement pulmonary valve. One such conduit 202 comprises a bovine jugular vein with a trileaflet venous valve preserved in buffered glutaraldehyde. Other valves are made of synthetic materials and are attached to the wall of the lumen of the conduit. The conduits may also include materials having a high X-ray attenuation coefficient (radiopaque materials) that are woven into or otherwise attached to the conduit, so that it can be easily located and identified.

Figure 2A:
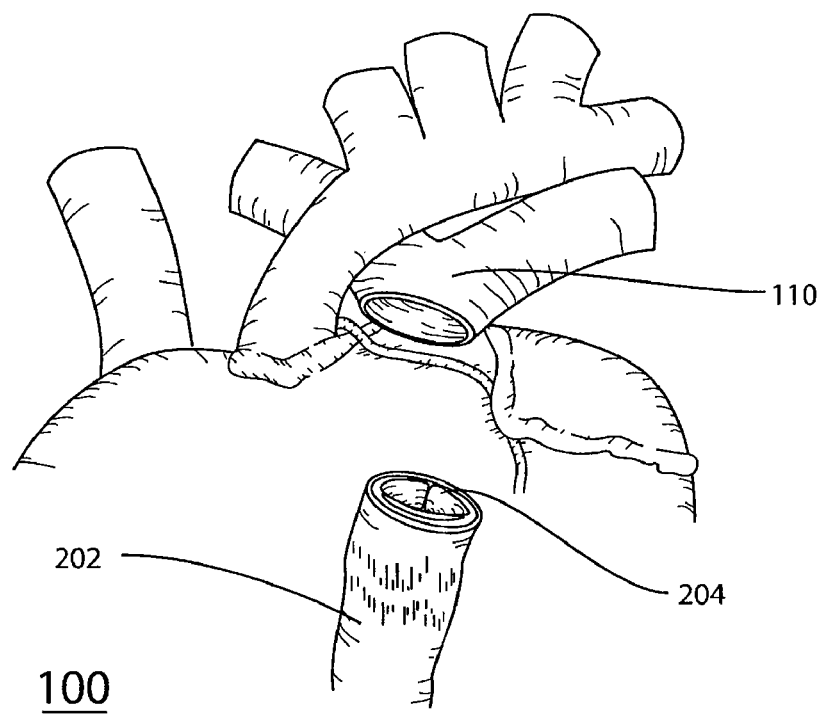
FIG. 2A is a schematic view showing the placement of a pulmonary conduit, as is known in the prior art.
Figure 2B:
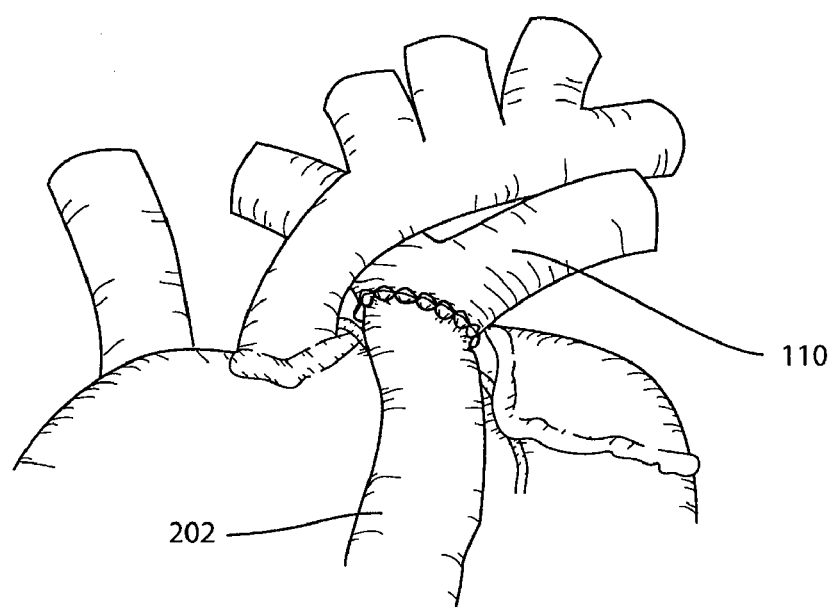
FIG. 2B is a schematic view showing attachment of a pulmonary conduit to the pulmonary artery, as is known in the prior art.
Figure 2C:
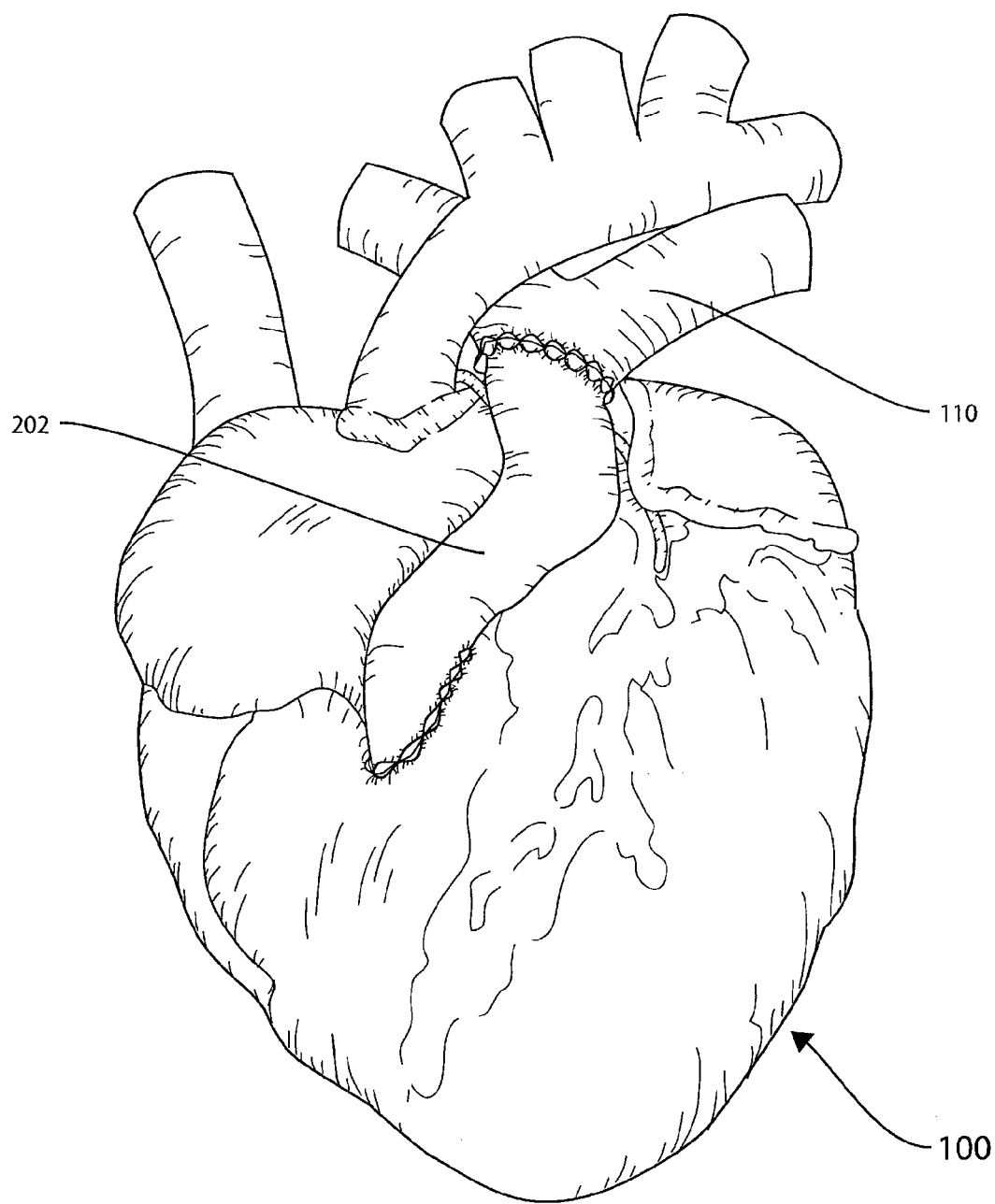
FIG. 2C is a schematic view showing attachment of a pulmonary conduit to the heart, as is known in the prior art.

As shown in FIGS. 2A and 2B, conduit 202, which houses valve 204 within its inner lumen, is installed within a patient by sewing the distal end of conduit 202 to pulmonary artery 110, and, as shown in FIG. 2C, attaching the proximal end of conduit 202 to heart 100 so that the lumen of conduit 202 connects to right ventricle 116.

Over time, implanted prosthetic conduits and valves are frequently subject to calcification, causing the affected conduit or valve to lose flexibility, become misshapen, and lose the ability to function effectively. Additional problems are encountered when prosthetic valves are implanted in young children. As the child grows, the valve will ultimately be too small to handle the increased volume of blood flowing from the heart to the lungs. In either case, the valve needs to be replaced.

The current invention discloses devices and methods for percutaneous catheter based placement of stented valves for regulating blood flow through a pulmonary artery. In a preferred embodiment, the valves are attached to an expandable support structure and they are placed in a valved conduit that is been attached to the pulmonary artery, and that is in fluid communication with the right ventricle of a heart. The support structure can be expanded such that any pre-existing valve in the conduit is not disturbed, or it can be expanded such that any pre-existing valve is pinned between the support structure and the interior wall of the conduit.

The delivery catheter carrying the stented valve is passed through the venous system and into a patient's right ventricle. This may be accomplished by inserting the delivery catheter into either the jugular vein or the subclavian vein and passing it through superior vena cava into right atrium. The catheter is then passed through the tricuspid valve, into right ventricle, and out of the ventricle into the conduit. Alternatively, the catheter may be inserted into the femoral vein and passed through the common iliac vein and the inferior vena cava into the right atrium, then through the tricuspid valve, into the right ventricle and out into the conduit. The catheters used for the procedures described herein may include radiopaque markers as are known in the art, and the procedure may be visualized using fluoroscopy, echocardiography, ultrasound, or other suitable means of visualization.

Figure 3A:
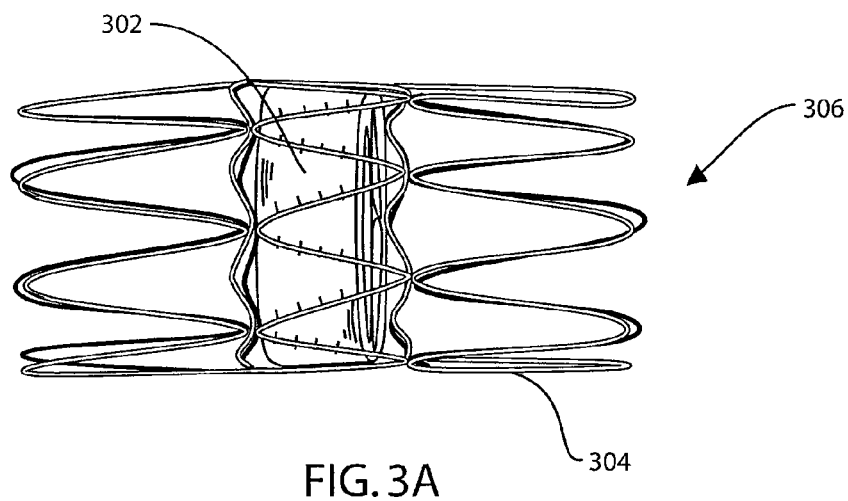
FIG. 3A is a cross sectional side view of a prosthetic pulmonary valve connected to a stent as is known in the prior art.

The current invention discloses devices and methods for percutaneous catheter based placement of stented valves such as stented valve 306, shown in FIG. 3A, for regulating blood flow through a pulmonary artery. In a preferred embodiment, shown in FIG. 3A, the valve, such as valve 302, is attached to an expandable support structure 304. The stented valve is placed in a valved conduit that has been attached to pulmonary artery 122, and that is in fluid communication with right ventricle 116 of heart 100. Support structure 304 can be expanded such that any pre-existing valve in the conduit is not disturbed, or it can be expanded such that any pre-existing valve is pinned between the support structure and the interior wall of the conduit.

One embodiment of a stented valve suitable for use in the present invention is disclosed in U.S. Pat. No. 5,957,949 titled "Percutaneous Placement Valve Stent" to Leonhardt, et al., which is assigned to the same assignee as the present application. The contents of the '949 Patent are hereby incorporated by reference.

Figure 3B:
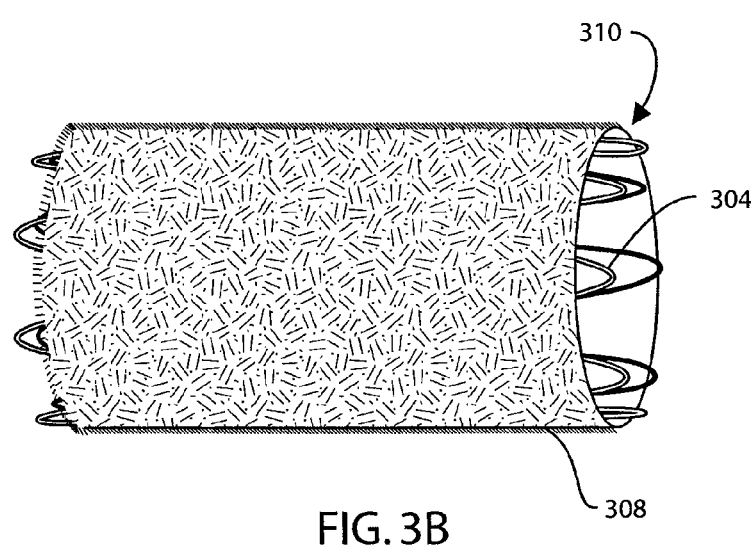
FIG. 3B is a schematic view of a stented valve with a barrier member disposed about the exterior surface of the stent portion, in accordance with the present invention.
Figure 3C:
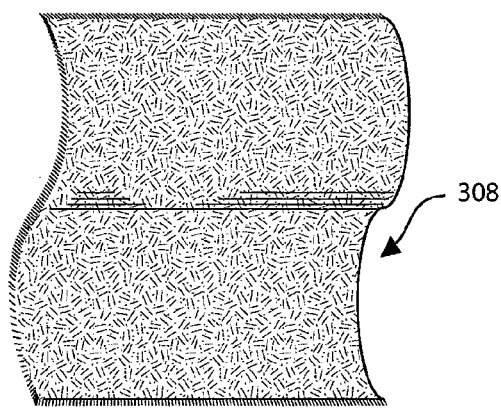
FIG. 3C is a schematic view of a pliable barrier material for covering the outer surface of a prosthetic valve device, in accordance with the present invention.

After a conduit has been implanted, it may become calcified or stretch over time. This stretching or calcification can result in a treatment site that is not round and symmetrical. This often results in an inadequate seal between the exterior surface of stented valve 306 and the wall of the conduit or vessel. One embodiment of the invention is stented valve 310, shown in FIG. 3B, in which the exterior surface of stented valve 306 has been covered with a flexible barrier material 308, shown in FIG. 3C. In one embodiment, barrier material 308 comprises directionally oriented microfibers attached to the surface of stented valve 310 and extending outward. The microfibers comprise biostable materials such as carbon, silica, polyester, nylon, polyamides, polyolefins, polyurethanes and combinations of these and other materials. In one embodiment of the invention, the microfibers are attached to a thin, pliable film or fabric that forms a covering layer over the exterior of stent portion 304 of replacement valve 310. The film comprises polyamide, polyurethane, polyimide, polytetrafluroethylene (PTFE), fluorinated ethylene propylene, a fabric of woven polyester fibers such as Dacron® fibers (E.I. Du Pont De Nemours & Co., Inc.), or other medically acceptable polymers. The microfibers are attached to the film by bonding or with an adhesive. In one embodiment, the microfibers are formed integrally with the film or fabric. When stented valve 310 is positioned at the treatment site within the lumen of conduit 202 or a vessel, the directionally oriented microfibers extend outward and contact the interior wall of the conduit and form a barrier that prevents blood from flowing around stented valve 310, between the outer surface of the stented valve and the inner wall of the conduit. The microfibers also press against the interior surface of the wall of conduit 202 and exert a small but significant force that is sufficient to prevent stented valve 310 from migrating along the length of conduit 202.

In another embodiment of the invention, barrier member 308 is a foam matrix that is readily compressible. The foam matrix comprises one or more materials such as open cell sponge, polyurethane foam, collagen polyvinyl alcohol, and poly(2-hydroxyethyl methacrylate). In one embodiment of the invention, the foam is compressed in the dry state, and expands as it absorbs water or bodily fluids. Stented valve 310 covered with a compressible foam barrier is delivered to the treatment site in the dry compressed state, and when it is positioned in the lumen of conduit 202 within the vascular system and exposed to blood or other aqueous bodily fluids, the foam absorbs fluid, expands, and fills the space between stented valve 310 and the interior wall of conduit 202 thus forming a barrier that prevents blood flow around valve 310 between the outer surface of the stented valve and the inner wall of the conduit. The expanded foam exerts sufficient force on the wall to maintain stented valve 310 in a fixed position at the treatment site.

In another embodiment of the invention, the barrier member comprises polyester batting adhered to the exterior surface of stented valve 310. Polyester batting is a disordered array of polyester microfibers that forms a soft, compressible mass. When stented valve 310 is positioned within the lumen of conduit 202, the polyester batting expands and presses against the wall of conduit 202 and forms a barrier to blood flow around valve 310. In addition, the polyester batting exerts sufficient force on the wall of conduit 202 to prevent stented valve 310 from migrating along the conduit.

Figure 4:
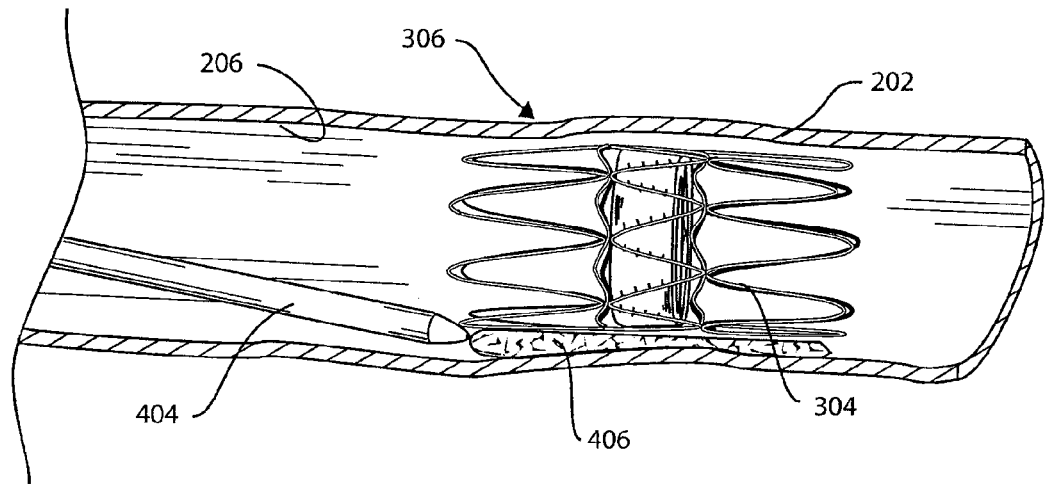
FIG. 4 is a schematic view of a prosthetic valve device situated in a conduit and a helical barrier material being deployed from a catheter, in accordance with the present invention.

In one embodiment of the invention, the barrier material is not attached to the exterior of stented valve 310, but instead, is deployed from the delivery catheter and positioned around the exterior surface of a valve such as stented valve 306 after stented valve 306 has been positioned at the treatment site in the lumen of conduit 202, (FIG. 4). In this embodiment, the barrier comprises, for example, flexible helical coil 406 made of one or more medically acceptable materials. Appropriate materials include, but not limited to, platinum, nitinol, platinum-iridium alloy, other platinum alloys, polyvinyl acid, polyvinyl pyrolidone and collagen. The helical coils may be of varying length and diameters, and may include radiopaque markers to facilitate accurate placement of helical barrier material 406.

As shown in FIG. 4, to deploy helical barrier material 406 from delivery catheter 404, the distal tip of catheter 404 is placed adjacent to the space between stented valve 306 and the surface of inner wall 206 of conduit 202. Helical barrier material 406 is delivered from the distal tip of catheter 404 and injected between exterior surface 304 of stented valve 306 and the interior surface of conduit 202. Helical barrier material 406 forms a cage-like, open structure that fills the space between stented valve 306 and the surface of the interior wall of conduit 202. Blood flow through the cage-like structure formed by helical barrier material 406 is slowed, and a blood clot forms that fills the intervening space and provides a barrier to further blood flow. In addition, the framework provided by helical barrier material 406 has sufficient mechanical strength to support stented valve 306 and prevent it from moving out of position at the target site.

Figure 5:
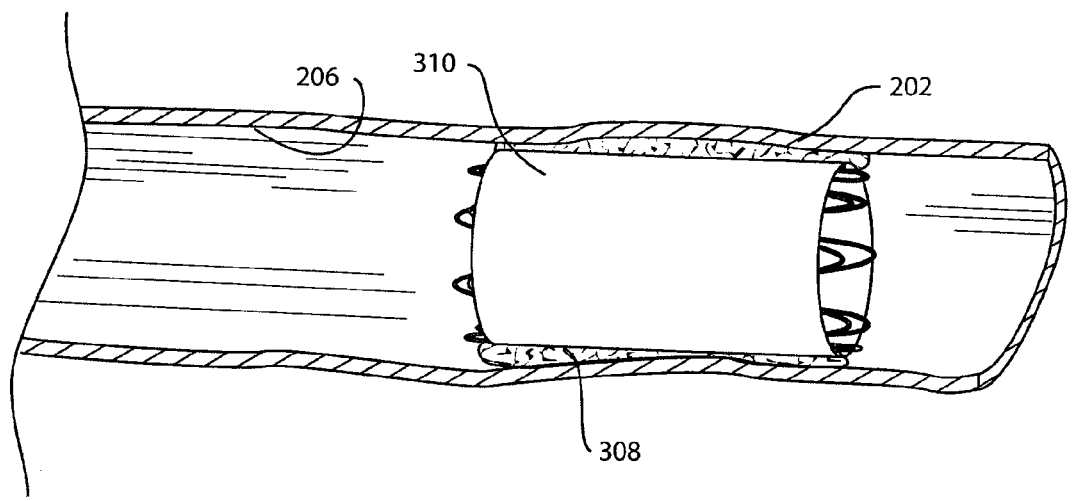
FIG. 5 is a schematic view of a prosthetic valve device with situated in a conduit and an expandable barrier that prevents blood flow between the valve device and the wall of the conduit, in accordance with the present invention.

FIG. 5 is a schematic view of a stented valve 310 or 306 positioned at the treatment site within the lumen of conduit 202 with a barrier disposed about the exterior surface of the valve device. The barrier may be a barrier member such as barrier material 308 that is attached to exterior surface 304 of stented valve 310, or, as in the case of the helical coil barrier, it may be positioned around valve device 306 after valve device 306 is situated at the treatment site. In either case, if the lumen of conduit 202 is not symmetrical and precisely complementary to the exterior surface of the valve device, barrier material 308 or 406 fills the space between the exterior surface of valve device 306 or 310 and the wall 206 of conduit 202. The barrier material prevents blood flow around the exterior surface of implanted valve 306 or 310 and prevents the valve device from moving from a fixed location at the treatment site and migrating along the length of conduit 202.

Figure 6:
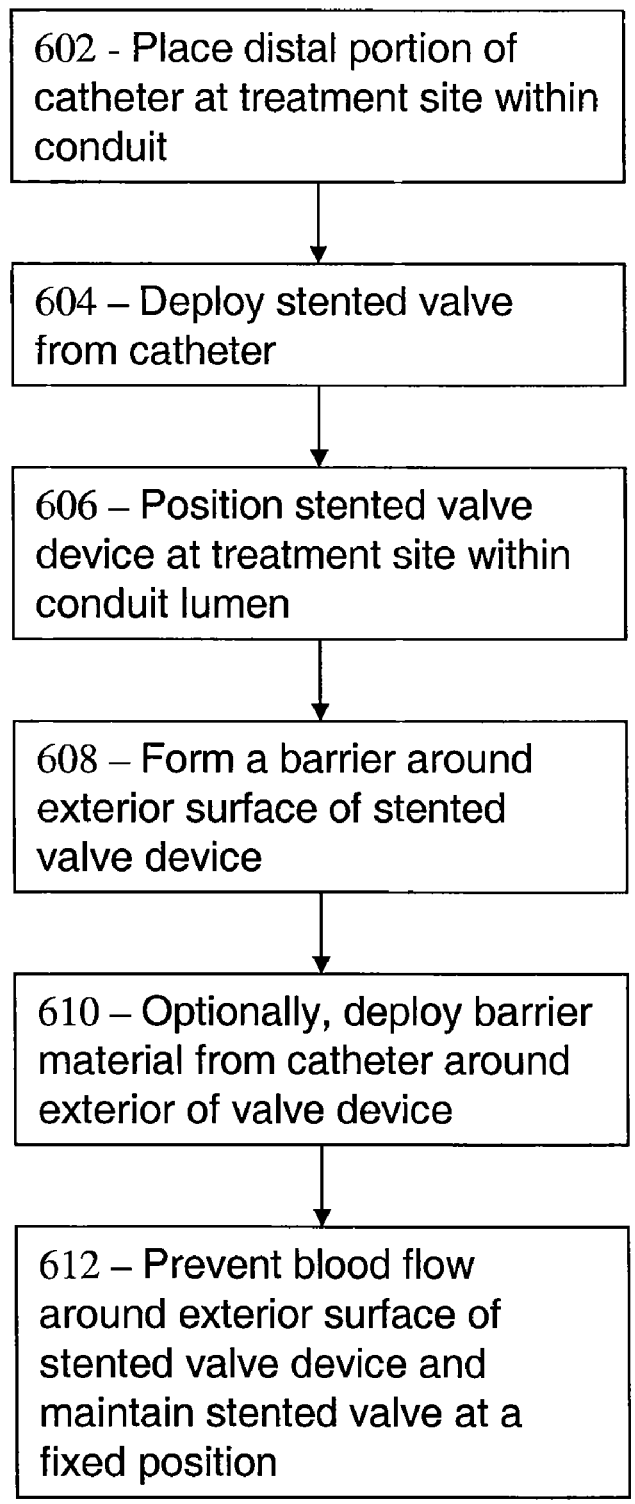
FIG. 6. is a flow diagram of a method of treating right ventricular outflow tract abnormalities by replacing a pulmonary valve with a stented valve and a barrier, in accordance with the present invention.

FIG. 6 is a flowchart illustrating method 600 for treating right ventricular outflow tract abnormalities by replacing a pulmonary valve in a nonsymmetrical region of a conduit, and using a barrier to prevent blood flow around the periphery of the replacement valve, in accordance with the present invention. Beginning at Block 602, a stented valve such as valve 306 or 310 is mounted on a delivery catheter such as catheter 404. The distal portion of delivery catheter 404 is then passed through the venous system and into a patient's right ventricle 116. This may be accomplished by inserting delivery catheter 404 into either the jugular vein or the subclavian vein, and passing it through the superior vena cava into right atrium 118. The catheter is then passed through tricuspid valve 104, into right ventricle 116, and out of the ventricle into conduit 202. Alternatively, delivery catheter 404 may be inserted into the femoral vein and passed through the common iliac vein and the inferior vena cava into right atrium 118, then through tricuspid valve 104, into right ventricle 116, and out into conduit 308. The catheters used for the procedures described herein may include radiopaque markers as is known in the art, and the procedure may be visualized using fluoroscopy, echocardiography, ultrasound, or other suitable means of visualization.

Next, stented valve device 306 or 310 is deployed from catheter 404 (Block 604), and positioned at the treatment site within conduit 202 (Block 606).

As indicated in Block 608, a barrier is then formed around the exterior surface of either stented valve device 306 or 310. In the case of stented valve device 310, barrier member 308 is attached to, and disposed about, at least a portion of the exterior surface of stented valve 310. Barrier member 308, for example directionally oriented microfibers or a layer of compressible foam, contacts the interior wall of conduit 202 and forms a barrier to blood flow. In one embodiment of the invention, barrier member 308 is a compressible foam that absorbs bodily fluid and expands and forms a barrier by filling the space between stented valve 310 and the interior wall of conduit 202. In one embodiment, stented valve device 306 is positioned within conduit 202, and a flexible coil barrier material 406 is injected between the exterior of stented valve device 306 and the wall of conduit 202. Blood trapped within the matrix formed by helical coil material 406 clots and forms a barrier to blood flow. In any of the above embodiments, the barrier around the exterior of stented valve device 306 or 310 prevents blood flow around the exterior surface of stented valve device 306 or 310, and maintains stented valve 306 or 310 in a fixed position, by preventing the valve device from migrating along the length of the conduit as indicated in Block 614.

While the invention has been described with reference to particular embodiments, it will be understood by one skilled in the art that variations and modifications may be made in form and detail without departing from the spirit and scope of the invention.

What is claimed is:

1. A vascular valve replacement system, the system comprising:
    an implantable conduit having a conduit wall;
    a catheter;
    a prosthetic valve device including a valve connected to a support structure, the valve device disposed on the catheter; and
    a barrier member disposed about an outer surface of the support structure of the valve device, the barrier member comprising a layer of material that will fill space between the valve support structure and the conduit wall when the support structure is deployed in the implantable conduit, wherein the barrier member comprises directionally oriented microfibers and wherein the directionally oriented microfibers comprise a material selected from a group consisting of carbon, silica, polyester, nylon, polyamides, polyolefins, polyurethanes, and mixtures thereof,
    wherein when the prosthetic valve device is deployed from the catheter in the implantable conduit, the barrier member prevents blood flow between the conduit and the outer surface of the support structure of the valve device.

2. A vascular valve replacement system, the system comprising:
    an implantable conduit having a conduit wall;
    a catheter;
    a prosthetic valve device including a valve connected to a support structure, the valve device disposed on the catheter; and
    a barrier member disposed about an outer surface of the support structure of the valve device, the barrier member comprising a layer of material that will fill space between the valve support structure and the conduit wall when the support structure is deployed in the implantable conduit, wherein the barrier member comprises polyester batting, wherein when the prosthetic valve device is deployed from the catheter in the implantable conduit, the barrier member prevents blood flow between the conduit and the outer surface of the support structure of the valve device.

3. A vascular valve replacement system, the system comprising:

an implantable conduit having a conduit wall;

a catheter;

a prosthetic valve device including a valve connected to a support structure, the valve device disposed on the catheter; and a barrier member disposed about an outer surface of the support structure of the valve device, the barrier member comprising a layer of material that will fill space between the valve support structure and the conduit wall when the support structure is deployed in the implantable conduit, wherein the barrier member is a compressible foam matrix, and wherein the compressible foam matrix comprises a material selected from a group consisting of open cell sponge, polyurethane foam, collagen, polyvinyl alcohol, and poly (2-hydroxyethyl methacrylate), wherein when the prosthetic valve device is deployed from the catheter in the implantable conduit, the barrier member prevents blood flow between the conduit and the outer surface of the support structure of the valve device.

4. The system of claim 3 wherein the volume of the compressible foam matrix increases upon exposure to water.

5. The system of claim 3 wherein the barrier member prevents the valve device from migrating along the length of the conduit.

6. A pulmonary valve replacement system, the system comprising:

an implantable conduit having a lumen defined by an inner wall;

a catheter;

a prosthetic valve device including a valve connected to a support structure, the valve device positioned in the conduit, and a barrier disposed about at least a portion of an outer surface of the support structure, wherein the baffler is deployed via the catheter between the inner wall of the conduit and the outer surface of the support structure of the valve device to prevent blood flow there between and wherein the barrier is a helical coil.

7. The system of claim 6 wherein the helical coil comprises one or more materials selected from a group consisting of platinum, nitinol, platinum-iridium alloy, polyvinyl acid, polyvinyl pyrolidone and collagen.

8. The system of claim 6 wherein the helical coil promotes blood clotting between the inner wall of the conduit and at least a portion of the outer surface of the support structure.

9. A method for replacing a pulmonary valve, the method comprising:

delivering a prosthetic valve device including a valve connected to a support structure having a barrier disposed about at least a portion of an outer surface of the support structure to a treatment site within an implantable conduit via catheter;

deploying the prosthetic valve device from the catheter;

positioning the prosthetic valve device within the implantable conduit;

forming a barrier around the outer surface of the support structure; and preventing blood flow around the support structure via the barrier and wherein forming a barrier further comprises increasing the volume of the barrier member by expanding a foam matrix.

10. A method for replacing a pulmonary valve, the method comprising:

delivering a prosthetic valve device including a valve connected to a support structure having a barrier disposed about at least a portion of an outer surface of the support structure to a treatment site within an implantable conduit via catheter;

deploying the prosthetic valve device from the catheter;

positioning the prosthetic valve device within the implantable conduit;

forming a barrier around the outer surface of the support structure; and preventing blood flow around the support structure via the barrier and wherein forming a barrier further comprises deploying the barrier material from a catheter and placing the barrier material between the outer surface of the support structure and the inner wall of the conduit.

11. The method of claim 10 further comprising preventing the prosthetic valve from migrating along the length of the conduit.

12. The method of claim 10 wherein forming a barrier around the outer surface of the support structure maintains the prosthetic valve in a fixed position that is perpendicular to the direction of blood flow within the vascular conduit and thereby improves the functioning of the valve.

* * * * *

UNITED STATES PATENT AND TRADEMARK OFFICE
CERTIFICATE OF CORRECTION

PATENT NO. : 7,524,331 B2
APPLICATION NO. : 11/278925
DATED : April 28, 2009
INVENTOR(S) : Birdsall Page 1 of 1

It is certified that error appears in the above-identified patent and that said Letters Patent is hereby corrected as shown below:

Column 9, line 44, "the baffler" should be changed to -- the barrier --

Signed and Sealed this

Tenth Day of November, 2009

David J. Kappos
*Director of the United States Patent and Trademark Office*